United States Patent [19]

Buschmann et al.

[11] Patent Number: 5,779,651
[45] Date of Patent: Jul. 14, 1998

[54] MEDICAL APPARATUS FOR THE DIAGNOSIS OF CARTILAGE DEGENERATION VIA SPATIAL MAPPING OF COMPRESSION-INDUCED ELECTRICAL POTENTIALS

[75] Inventors: Michael D. Buschmann, Montreal; Robert Guardo, Mt-St-Hilaire; Martin Garon; Pierre Le Guyader, both of Montreal; Pierre Savard, Ste-Thérése, all of Canada

[73] Assignee: Bio Syntech, Laval, Canada

[21] Appl. No.: 796,299

[22] Filed: Feb. 7, 1997

[51] Int. Cl.$^6$ .................................................. A61B 5/103
[52] U.S. Cl. ............................................. 600/587; 600/300
[58] Field of Search .................................. 128/774, 639, 128/749

[56] References Cited

U.S. PATENT DOCUMENTS 5,246,013  9/1993  Frank et al. .

5,503,162  4/1996  Athanasiou et al. .

FOREIGN PATENT DOCUMENTS

PCT/FI92/00220  7/1992  WIPO .

Primary Examiner—Scott M. Getzow
Attorney, Agent, or Firm—Klauber & Jackson

[57] ABSTRACT

The present invention relates to a medical apparatus for the early detection and the diagnosis of cartilage degeneration and a method for using such apparatus. The apparatus comprises at least two point electrodes, a signal processor located in proximity of the electrodes, a defined abutment in recess of the electrodes for allowing compression of the cartilage against the electrodes until the cartilage abuts against the abutment surface and a computer program for analyzing and interpreting the data received from the electrodes. The medical apparatus may be used in research to identify effects of new compounds or drugs on the cartilage or may be used in clinics to monitor the degradation of cartilage of a patient over an extended period of time.

19 Claims, 6 Drawing Sheets

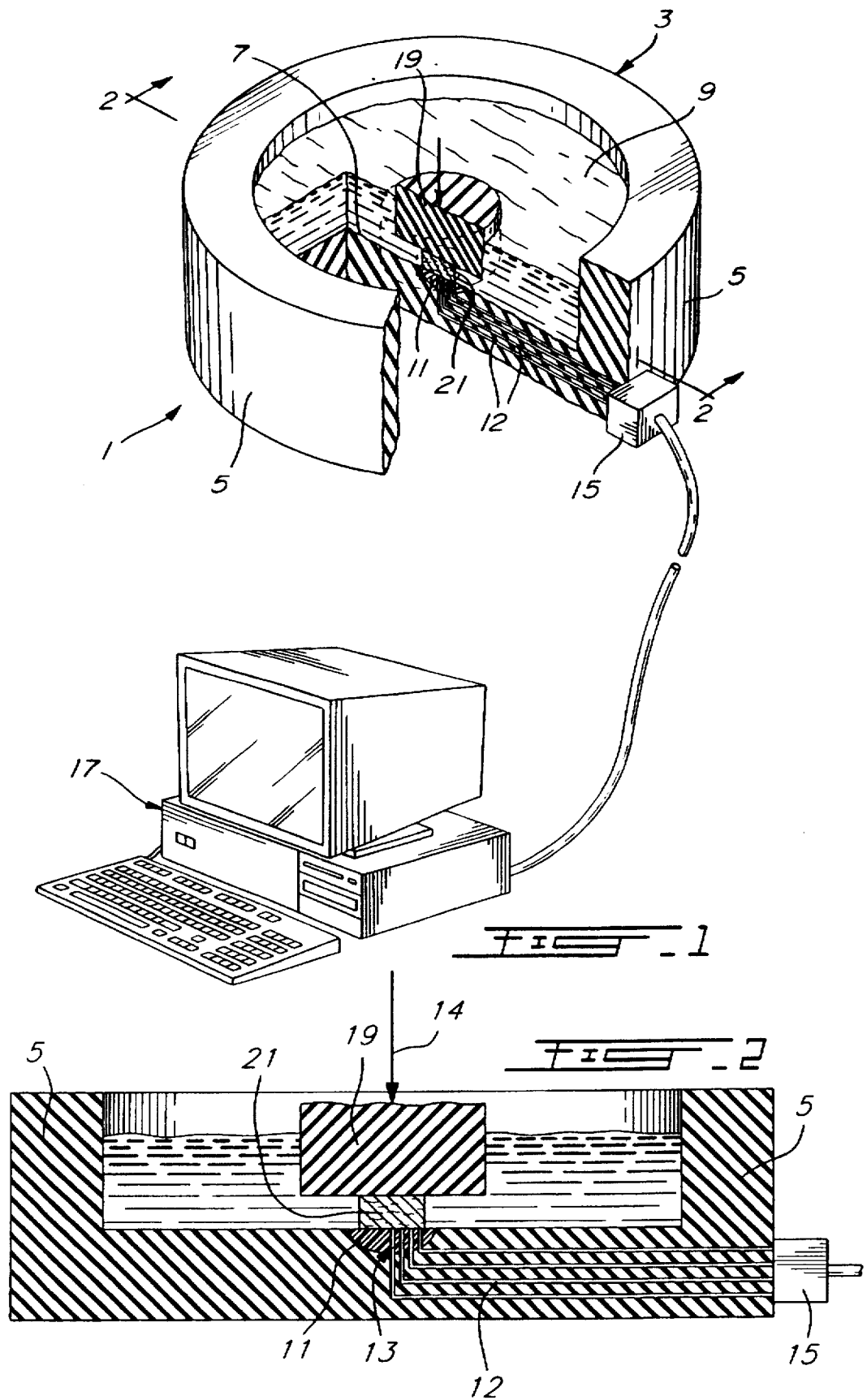

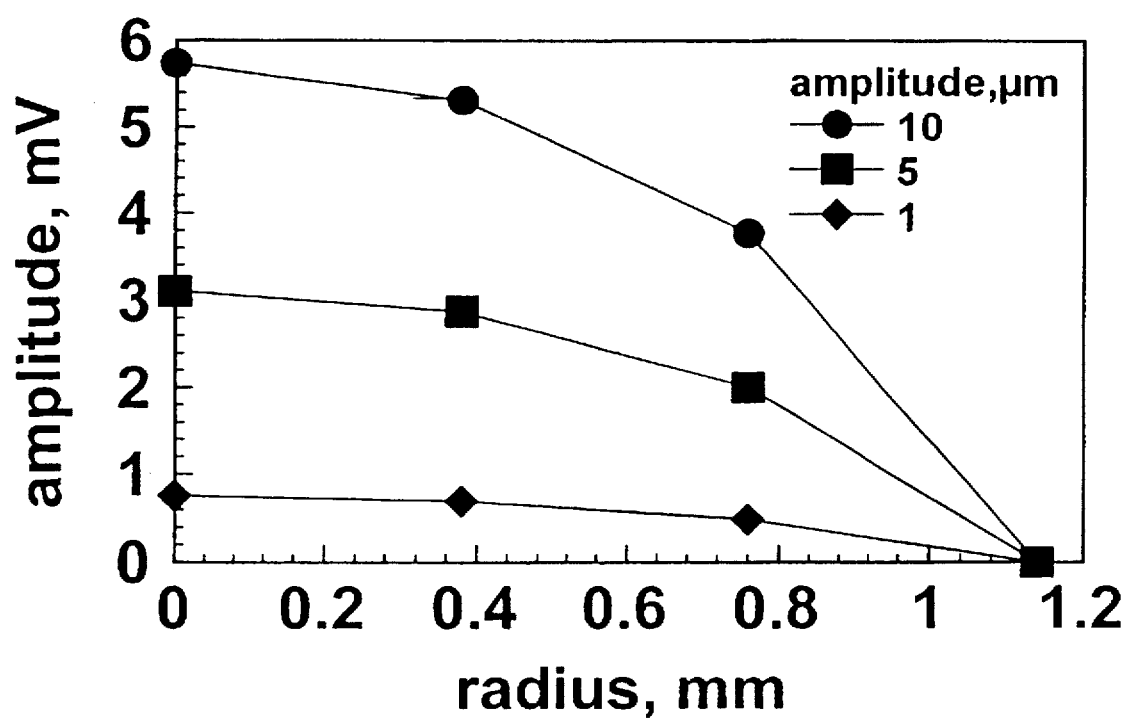
FIG_5

MEDICAL APPARATUS FOR THE DIAGNOSIS OF CARTILAGE DEGENERATION VIA SPATIAL MAPPING OF COMPRESSION-INDUCED ELECTRICAL POTENTIALS

BACKGROUND OF THE INVENTION (a) Field of the Invention

The present invention relates to a medical apparatus for early detection and diagnosis of cartilage degeneration and a method for using such apparatus.

(b) Description of Prior Art

The physical and biochemical degeneration of articular cartilage constitutes the hallmark of several diseases of the joint including osteoarthritis (OA) and rheumatoid arthritis. Several of these degenerative joint processes are slow but progressive, requiring several years or decades to attain a symptomatic state which can only then be currently diagnosed using radiological and arthroscopic techniques. Unfortunately, the tissue damage accrued during this long period of progressive degeneration appears to be essentially irreversible, rendering the sole treatment of such conditions to be joint replacement. These costly treatments in themselves are of transitory benefit and may have to be repeated several times throughout the lifetime of the patient. One primary reason for the near exclusive use of radical and partial treatments such as joint replacement is the lack of diagnostic tools capable of detecting cartilage degeneration in the early and potentially reversible stages.

The most prevalent and costly joint disorder, osteoarthritis (OA), is currently diagnosed at a late stage based on physical examination (pain, swelling, deformity, joint enlargement, limitation of motion, osteophyte formation), X-ray and magnetic resonance imaging (MRI), which is a radiologic imaging (joint space narrowing, reduced cartilage thickness, osteophyte formation, subchondral bone sclerosis), and by visual arthroscopy (cartilage fissuring, fibrillation, local erosion). Proposed methods for early detection and follow-up of cartilage degeneration in osteoarthritis (OA) have been based on serum and synovial fluid molecular markers, refined MRI, and evaluation of cartilage mechanical properties (International Application published under the publication number WO 93/02619 in the name of Kiviranta and Jurvelin and U.S. Pat. No. 5,503,162 in the name of Athanasiou et al.) or electromechanical properties (U.S. Pat. No. 5,246,013 in the name of Frank et al.) via non-visual arthroscopic apparatus. These proposed early detection methods are still in development and none has reached the stage of widespread clinical application.

Since the role of articular cartilage is primarily physical in transmitting forces of articular cartilage to bone and in providing low friction joint surfaces, it is attractive to develop diagnostic tools which directly reflect these functional physical properties. Biochemical markers and the various imaging modalities provide much information but none are specific for the qualities of joint articular cartilage necessary to fulfill its function.

Although information concerning the most important initial events in osteoarthritis is scarce, several studies have indicated cartilage weakening due to the degradation or loss of the two main molecular constituents, the large aggregating proteoglycan, aggrecan, and the highly cross-linked network of collagen fibrils. Typically a precipitous loss of aggrecan is one of the earliest detectable events in osteoarthritis. The ability of cartilage to withstand compressive forces is tightly linked to the entrapment of highly concentrated aggrecan within the collagen network. Aggrecan is a highly sulfated and carboxylated molecule, leading to the presence of a high concentration of ionized negative charge groups covalently linked to the macromolecule. Compressive stiffness of cartilage is therefore in a large part due to repulsive electrostatic forces present between the charged units of aggrecan. The loss of aggrecan in osteoarthritis represents a significant functional tissue injury.

The presence of a high concentration of ionized charge groups on aggrecan also gives rise to electromechanical transduction phenomena. Tissue compression convects interstitial fluid containing an excess of mobile positively charged counterions past the fixed negatively charged aggrecan to generate electrical fields and potentials, the latter being called streaming potentials. The amplitudes and dynamics of these electromechanical phenomena reflect the physical function of cartilage, with special reference to the contribution of aggrecan.

SUMMARY OF THE INVENTION

One feature of the present invention is to provide a medical apparatus for early detection of cartilage degradation.

Another feature of the present invention is to provide a medical apparatus for use in fundamental research on progressive degeneration of cartilage and treatments thereof, allowing monitoring of tissue health during extended periods of time.

Another feature of the present invention is to provide an artroscopic apparatus for mechanical and electromechanical evaluation of articular cartilage.

Another feature of the present invention is to provide an electromechanical diagnostic apparatus based on a direct evaluation of physical function with particular sensitivity to the most labile and dynamic molecular component in osteoarthritis, that is aggrecan, allowing for an early diagnosis and follow-up of the disease.

The above features, from a broad aspect of the present invention, provide a medical apparatus for early detection of degradation in cartilage. The medical apparatus comprises at least two spaced apart electrodes fixed to a solid surface, signal processing means for processing signals received from the electrodes, means for compressing said electrodes and cartilage together and means for analytical interpretation of data received from said signal processing means. The electrodes are exposed for contacting with a cartilage to be analyzed. Each of the electrodes measures a streaming potential in the cartilage. The medical apparatus allows for spatially and temporally resolving the streaming potential measured between the electrodes.

The above features, still from a broad aspect of the present invention, provide an arthroscopic apparatus for early detection of degradation in cartilage. The arthroscopic apparatus comprises at least two platinum point electrodes, immobilized on a solid surface for measuring the streaming potentials of cartilage, a front-end signal processor located in proximity of the electrode and comprising a voltage follower having a high input impedance and a low bias current to process signals received from the electrodes and maximize rejection of common-modes of measured differential voltages between adjacent electrodes, an abutment surface recessed from the electrodes for allowing the electrodes to be pressed in the cartilage until said cartilage abuts against the surface and means for analytical interpretation of data received from the processor for comparing the data received with other stored data obtained from given tissues affected by osteoarthritis at a given degree. The front-end signal processor reduces noise pick up and microphonic effects. The arthroscopic apparatus is sized and shaped to be introduced in an arthroscopic opening of about 2 to 6 mm of diameter and allows for spatially and temporally resolving the streaming potential between the electrodes.

The above features, still from a broad aspect of the present invention, also provide a method for detecting and mapping degradation in cartilage. The method comprises the steps of applying at least two electrodes against the cartilage, compressing the electrodes and the cartilage together, measuring a streaming potential at each of the electrodes, analyzing and resolving the streaming potentials measured to obtain a map thereof and interpolating the measured streaming potentials to determine the condition of the cartilage. The method may further comprise the step of comparing the measured streaming potentials with stored streaming potentials.

The potentials measured with the apparatus in accordance with the present invention directly reflect articular cartilage function (unlike biochemical markers and imaging modalities). The electrical signals resulting from the measured potential are directly dependent on, and very sensitive to, the presence of one of the most labile and important molecules lost from cartilage in arthritis, that is aggrecan.

The small size of the point electrodes allows for ease of arthroscopic use and high resolution maps of streaming potentials. The maps may be resolved in two dimensions.

BRIEF DESCRIPTION OF THE DRAWINGS

Raving thus generally described the nature of the invention, reference will now be made to the accompanying drawings, showing by way of illustration a preferred embodiment thereof, and wherein:

FIG. 1 is a fragmentary perspective view of a medical apparatus for early detection and diagnosis of cartilage degeneration and constructed in accordance with a preferred embodiment of the present invention;

FIG. 2 is a vertical cross-section view partly schematic along lines 2—2 of FIG. 1;

FIG. 5 is a graph illustrating the effect of amplitude on signals measured with the apparatus of FIG. 1.

DETAILED DESCRIPTION OF THE INVENTION

Figures 3A, 3B, 3C, 3D, 3E:
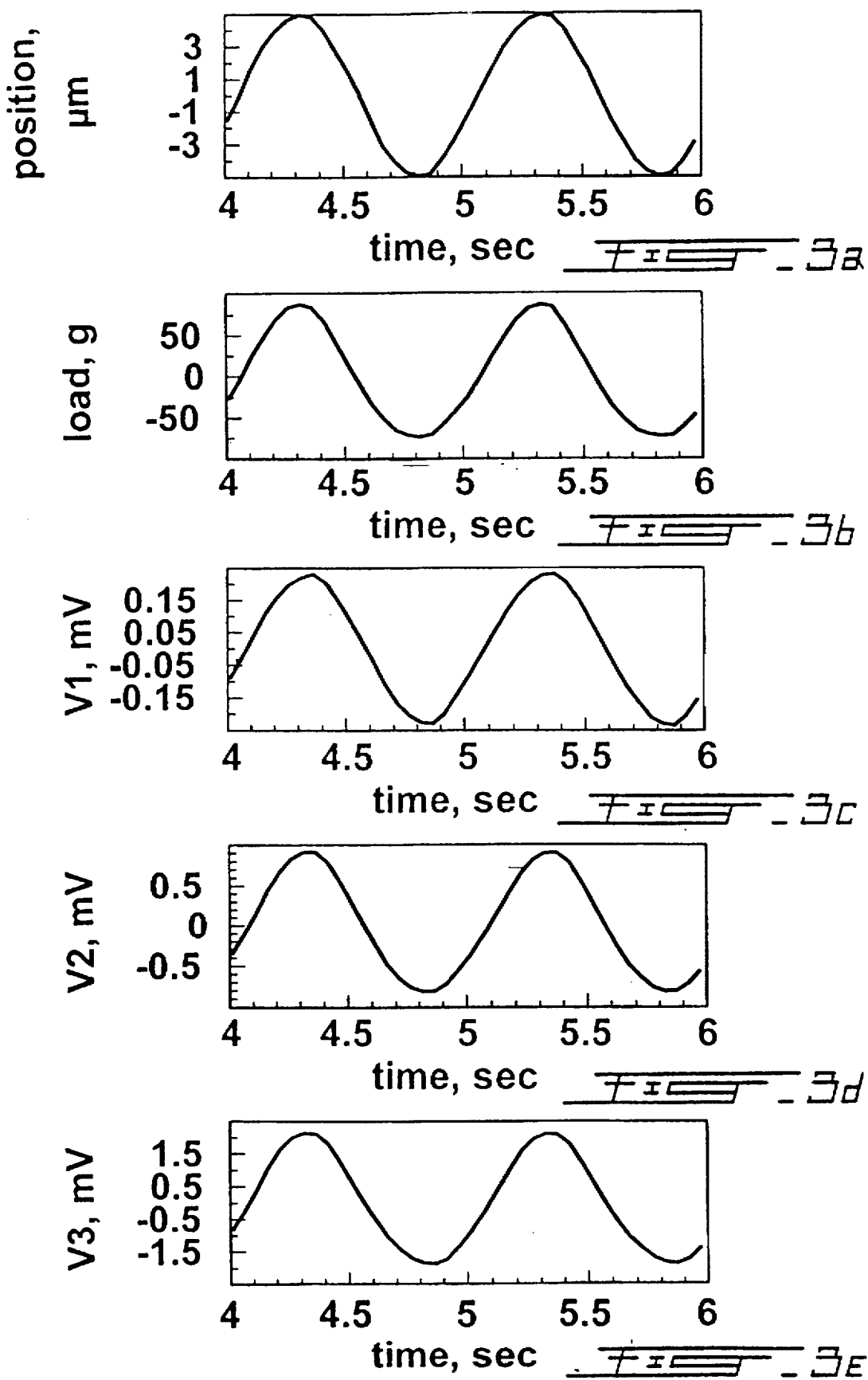
FIGS. 3a to 3e are graphs illustrating the value of the electrical signals measured with the apparatus of FIG. 1 and their spatial dependency.

In accordance with one embodiment of the present invention, there is provided a medical apparatus to detect progressive degeneration of cartilage. FIG. 1 illustrates a medical apparatus 1 that may be used in fundamental research to follow up in vitro degeneration of cartilage. This apparatus 1 may also be useful in assessing integrity of cartilage before, during or after treatment of that cartilage with drugs or chemical compounds, therefore allowing evaluation of the effects of drugs or chemical compounds on the cartilage.

The apparatus 1 illustrated in FIG. 1 comprises a vessel 3 defining an enclosure having four sidewalls 5 and a rigid bottom wall 7 for containing a liquid 9 therein. An epoxy cylinder 11 containing four electrodes 13 is located on the bottom wall 7 at the center of the vessel 3. The electrodes 13 are connected to a signal conditioning module 15, which is itself connected to a computer 17 for interpreting and analyzing the data received from the module 15. The apparatus 1, according to this embodiment of the invention, also comprises an actuator and a load cell 19 for applying a compression on a disk of cartilage 21 when the load cell 19 is positioned on the disk of cartilage, thereby producing a deformation of the cartilage 21.

The electrodes 13 are platinum wires 12 secured through a nylon mesh producing 50 µM diameter point electrodes. The platinum wires 12 are cast into the epoxy cylinder 11 and exposed as a linear array with a regular center-to-center distance of 380 µm (determined by the nylon mesh), covering a total distance of 1.14 mm. The cylinder 11 containing the electrodes 13 is fixed to the bottom wall 7 of the vessel 3. The exposed surfaces of the platinum electrodes 13, at the surface of the bottom wall 7 are further platinized using electrochemical deposition to reduce the contact impedance of the electrodes 13. Electrical signals from the electrodes 13 are passed through the signal conditioning module 15 before being received by the computer 17. The vessel 3 is mounted in a micromechanical testing apparatus comprising the load cell 19 which is fixed to a precision actuator (not illustrated) for precisely positioning the load cell 19 over the electrodes 13 at a given distance thereof, and applying, in use, a given pressure along arrow 14 on the cartilage 21 against the electrodes 13.

The electrodes 13, as described above, allow for a spatial resolution of the streaming potentials of the order of 0.38 mm, allowing to produce a streaming potential map. In order to allow for such a resolution, the electrodes 13 preferably have a diameter smaller than 500 µm and more preferably smaller than 100 µm. They may be point electrodes or circular electrodes. They could be made of other metals such as iridium or gold.

The minimal number of electrodes used in accordance with the present invention is two. When more than two electrodes are used, they may be placed in such a manner as to define more than one axis to evaluate and resolve streaming potentials spatially in more than one dimension, such as length and width for example.

The specialized signal conditioning module 15 is specifically designed for interfacing with the electrodes 13. The module 15 is mounted in proximity to the electrodes 13 to minimize noise pickup and microphonic effects. The signal conditioning module 15 may also be mounted further from the electrodes, provided that the electrodes are shielded to minimize noise pickup and microphonic effects.

Figure 9:
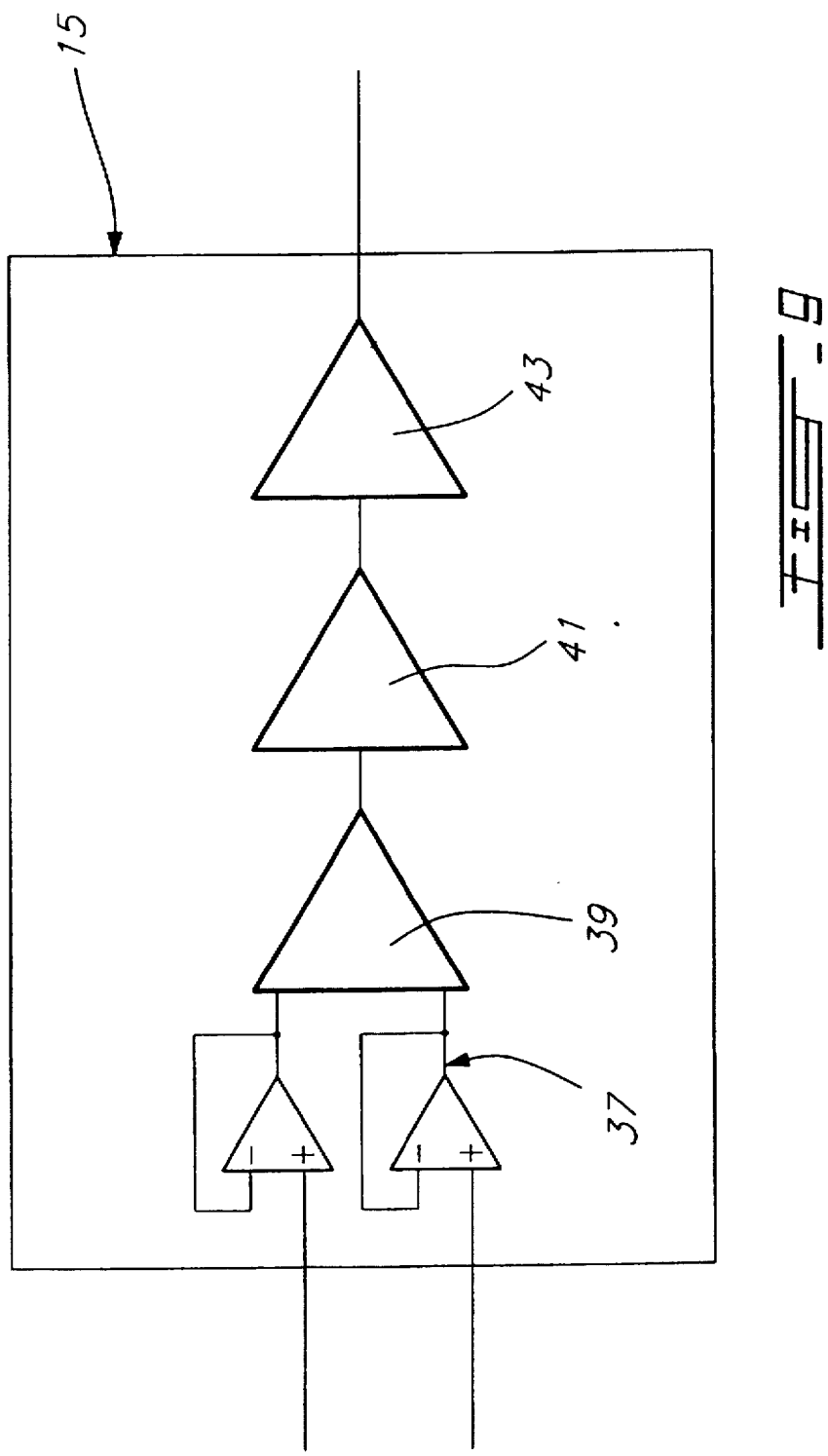
FIG. 9 is a block diagram of a signal processing module used in the apparatus comprising two electrodes.

FIG. 9 shows a block diagram of a module used in an apparatus comprising two electrodes. The module comprises a voltage follower 37, a low-pass filter 39, a high-pass filter 41 and an amplifier 43. The voltage follower has a high input impedance (>>100 Mohm; 5 pF) and low bias current (<1 pAmp) to maximize rejection of common-modes of measured differential voltages between adjacent electrodes. The high input impedance of the voltage follower is required due to the relatively high impedance of the interface between the platinum wires and the electrolyte milieu. The input impedance of the first stage of the signal conditioning module must be significantly higher than this contact impedance to avoid the effect of a voltage divider. However, too high an impedance in the voltage followers leads to environmental noise pickup and microphonic effects. Therefore, a precise balance between the electrode contact impedance and the noise pickup must be struck for the signals to be acquired. A minimal distance between the electrodes and the voltage follower is preferred to minimize noise pickup.

The precision actuator may be replaced by any means, such as an electromechanical, piezoelectric or manual means, for accurately supplying a defined compressive displacement of the electrodes surface into the cartilage.

The computer 17 uses an analytical method of data interpretation to correlate imposed compressive displacements and measured electrical potentials to the composition and structure of the cartilage under test. This method relies on detected temporal and spatial variations of the streaming potentials across the tissue surface. A characterization of normal maps and maps typical of tissue deterioration at various degree due to osteoarthritis will indicate the degree of health or disease of an unknown tissue.

The apparatus illustrated in FIGS. 1 and 2 may be used in research to evaluate effects of chemical compounds or drugs on the cartilage. To do so, pieces of normal or abnormal cartilage may be cut from humans or animal models and analyzed. The pieces may also be submitted in culture to the chemical compounds or drugs. In doing so, it is possible to identify new chemical compounds or drugs to be used for the treatment or prophylaxis of osteoarthritis.

Figure 6:
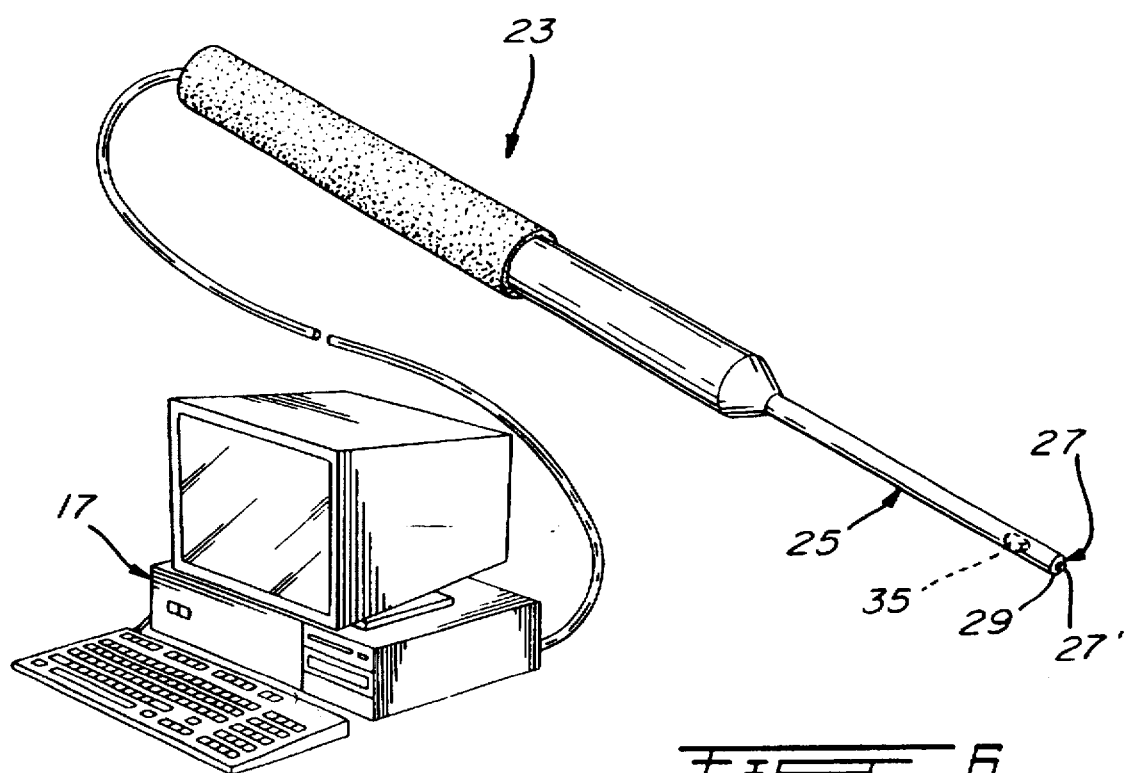
FIG. 6 is a perspective view of another embodiment of an apparatus in accordance with the present invention.

Another preferred embodiment is illustrated in FIG. 6. This second embodiment illustrates a clinical apparatus 23 to evaluate human articular cartilage function during an arthroscopy. The clinical apparatus 23 is embodied in a probe 25 resembling a pen. The probe 25 is connected to the computer 17 for data analysis. The probe 25 has a free end 27 provided with a tip 27' comprising point electrodes 33, an abutment surface 29 and the signal conditioning module 35 which is embedded in the tip 27', in close proximity of the electrodes 33.

Figure 7:
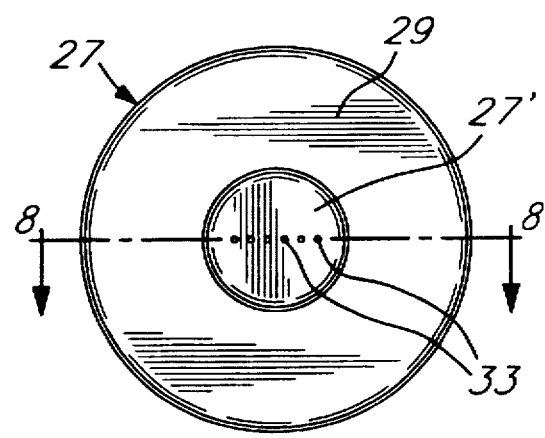
FIG. 7 is an enlarged end view illustrating a tip of a probe of an arthroscopic apparatus according to the other preferred embodiment of the apparatus of FIG. 6.
Figure 8:
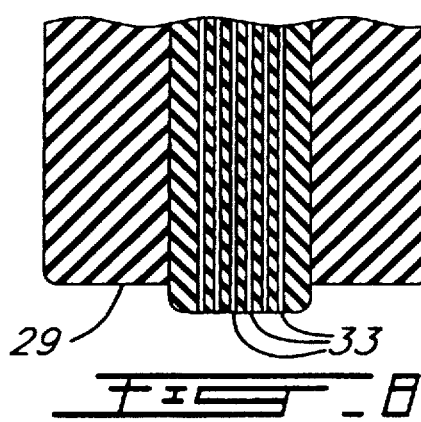
FIG. 8 is a fragmentary cross-section along lines 8—8 of the tip of FIG. 7.

FIG. 7 illustrates an end view of the free end 27 and the tip 27' of the probe 25. Six electrodes 33 are immobilized in an array in the tip 27'. The abutment surface 29 illustrated in FIG. 8 is recessed compared to the tip 27'. Accordingly, the abutment surface 29 is used to create a defined compressive displacement on the cartilage. The tip 27' is applied on, and pressed against the cartilage until the abutment surf ace 29 rests on the cartilage. At this point, the tip 27' and the protruding electrodes 33 effect a compression on the cartilage inducing a streaming potential and allowing to measure and map this streaming potential. The potential measured by the electrodes 33 is sent to the signal conditioning module 35 which relays the data to the computer 17, allowing for a comparison of the map of streaming potential of the analyzed cartilage with typical maps of known healthy tissues.

Since the size of the electrode array may be on the order of 1 mm, the overall diameter of the probe 25 of the clinical apparatus 23 which must be inserted into the joint can be much smaller than the arthroscopic opening (2-6 mm). The displacement of the electrodes is effected manually but precisely controlled by forcing the tip 27' into the cartilage until the abutment surface 29 stops the tip 27' from deforming the cartilage. Thus the type of applied displacement is predetermined by the step between the face of the tip and the abutment surface. The resulting electrical signals vary after the compressive force is applied as they tend to an equilibrium. The amplitude of these signals have been proven to be strongly dependent on the integrity of the cartilage by using a cytokine-mediated (interleukin-1) in vitro cartilage degradation model.

The present invention will be more readily understood by referring to the following example which is given to illustrate the invention rather than to limit its scope.

EXAMPLE I

Articular cartilage explants were isolated from a humeral head of a 1–2 year old steer. Disks of cartilage were cut from the explants. An articular cartilage disk was placed in the vessel 3 of the apparatus 1 illustrated in FIGS. 1 and 2. The vessel 3 was filled with 0.01 M NaCl. One of the electrodes 13 of the apparatus, located in the center of the cylinder, was placed in contact with the center of the articular disk, the other three electrodes being disposed across the first 1.14 mm of the 1.5 mm radius of the disk 21. After contacting the upper surface of the disk 21 with the load cell 19, a 240 µm static compression offset was applied in a sequence of small stepped compressions. Following equilibrium, a series of dynamic sinusoidal tests was performed using frequencies in the range 0.02 Hz to 2.0 Hz and amplitudes in the range 0.5 µm to 20 µm. Ten cycles were executed for each test and harmonic analysis of the signals was performed on the last 6 cycles.

An example of the raw data obtained with the apparatus of FIGS. 1 and 2 is shown in FIG. 3 for a test at a frequency of 1 Hz using a 5 µm displacement amplitude. FIGS. 3a to 3e illustrate the position, the load data and the differences of voltage present between three adjacent electrodes 13 contacting the articular disk surface 21, respectively. The voltage V1 is the streaming potential present between the center of the disk and 380 µm away from that center; voltage V2 is the next incremental streaming potential from 380 µm to 760 µm, and V3 is another incremental streaming potential from 760 µm to 1140 µm. The amplitude of the incremental streaming potential V1, V2 and V3 increases from the disk center to the periphery, demonstrating the inherent spatial variation of the electric field, induced by the actuator. A streaming potential radial profile can be constructed by taking the reference potential as that of the most peripheral electrode at 1.14 mm from the disk center 21. FIG. 3 illustrates the electrical signals obtained from the apparatus and their spatial dependence. The magnitude and phase of V1, V2 and V3 in FIGS. 3c to 3e depend on several factors including the geometry of the specimen, loading configuration, loading frequency and amplitude, content and distribution of charged species (aggrecan) in the tested issue, and degree of immobilization of aggrecan via entrapment in the collagen network. The ability to resolve streaming potentials on such a small spatial scale (<<1 mm) is an important aspect of the invention. Using this ability allows to discriminate between the factors listed above so that specific information on the distribution and content of aggrecan, and its immobilization in the collagen network can be obtained, providing for disease diagnosis.

Figure 4A:
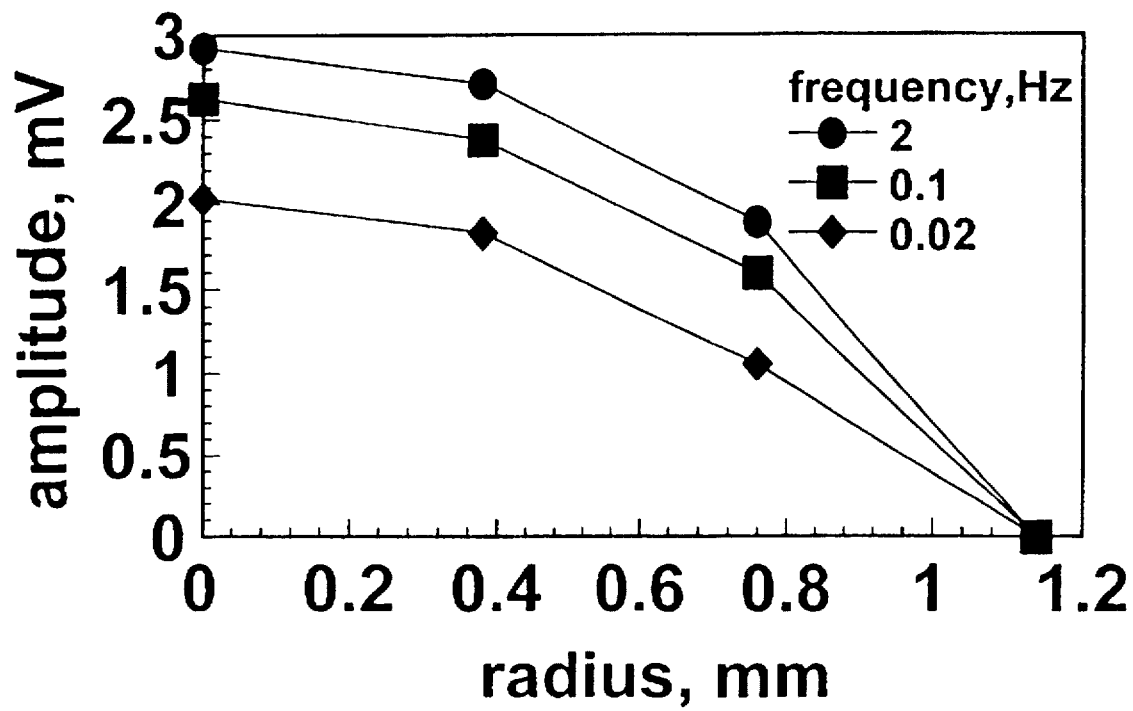
FIGS. 4a and 4b are graphs illustrating the effect of frequency on signals measured with the apparatus of FIG. 1.
Figure 4B:
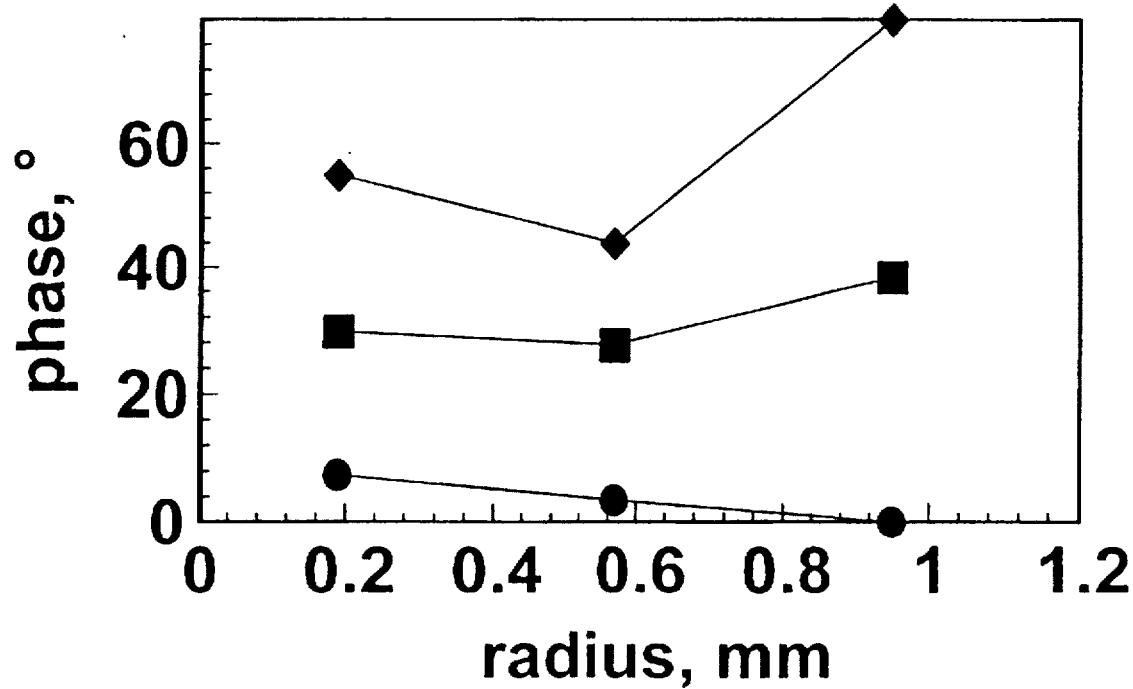

The amplitude and phase of the radial profile of the potential obtained with the apparatus of FIGS. 1 and 2 is shown in FIGS. 4a and 4b, respectively, for three different frequencies conducted at a 5 µm amplitude. The reference for the potential phase is the phase of the applied axial displacement (see FIG. 3a). FIGS. 4a, 4b and 5 illustrate the effects of frequency and amplitude on the measured signals for a healthy cartilage disk tested in the geometry of unconfined compression. FIG. 4a shows that the streaming potentials tend to increase in magnitude with higher frequencies. FIG. 4b shows that these streaming potentials tend to become more out of phase with the displacement at lower frequencies.

The amplitude of the radial streaming potential profile for three different displacement amplitudes at 1 Hz is shown in FIG. 5. These are the first spatially resolved (<1 mm resolution) measurements of streaming potential in loaded cartilage. FIG. 5 shows that the streaming potentials are approximately proportional to the applied displacement amplitude.

Further data have been analyzed having altered the state of health (integrity) of the tissue by culturing cartilage disks with interleukin-1. The cell-mediated interleukin-1-induced loss of aggrecan results in greatly diminished amplitudes of the measured streaming potentials.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A medical apparatus for early detection of degradation in cartilage, said apparatus comprising:
   a) at least two spaced apart point electrodes fixed to a solid surface and exposed for contact with a cartilage to be analyzed, each said electrodes measuring streaming potentials in such cartilage;
   b) means for compressing said electrodes and cartilage together;
   c) signal processing means for processing signals received from the electrodes; and
   d) means for analytical interpretation of data received from said signal processing means, and
   wherein said medical apparatus allows for spatially and temporally resolving the streaming potentials measured between said electrodes.

2. The medical apparatus of claim 1, wherein the electrodes are made of metal wires.

3. The medical apparatus of claim 1, wherein the processing means are in close proximity to the electrodes for reducing noise pick up and microphonic effects.

4. The medical apparatus of claim 1, wherein the electrodes are made of platinum.

5. The medical apparatus of claim 4, wherein the electrodes are point electrodes having a surface of platinum wire exposed to the cartilage, said exposed surface being treated to reduce electrical contact impedance.

6. The medical apparatus of claim 1, wherein the means for processing comprises a voltage follower having a high input impedance and a low bias current to maximize rejection of common-modes of measured differential voltages between adjacent electrodes.

7. The medical apparatus of claim 1, wherein the means for supplying a compressive displacement of the electrodes is selected from electromechanical, piezoelectric or manual means.

8. The medical apparatus of claim 1, wherein the electrodes have a diameter smaller than 500 μm.

9. The medical apparatus of claim 8, wherein the electrodes have a diameter smaller than 100 μm.

10. The medical apparatus of claim 1 comprising at least three electrodes, wherein said at least three electrodes define two dimensions from which data are to be analyzed.

11. The medical apparatus of claim 1, wherein the electrodes are capable of spatially resolving streaming potentials at a resolution of about 0.38 mm.

12. The medical apparatus of claim 1, wherein the metal wires are made of a metal selected from the group consisting of iridium, platinum and gold.

13. An arthroscopic apparatus for early detection of degradation in cartilage, said apparatus comprising:
   a) at least two platinum point electrodes, immobilized on a solid surface for measuring the streaming potentials of cartilage;
   b) an abutment surface recessed from the electrodes for allowing the electrodes to be pressed in the cartilage until said cartilage abuts against the surface;
   c) a front-end signal processor located in close proximity to the electrodes and comprising a voltage follower having a high input impedance and a low bias current to process signals received from the electrodes and maximize rejection of common-modes of measured differential voltages between adjacent electrodes, said processor reducing noise pick up and microphonic effects; and
   d) a means for analytical interpretation of data received from the processor for comparing the data received with other stored data obtained from given tissues affected by osteoarthritis at a given degree, and
   wherein said apparatus is sized and shaped to be introduced in an arthroscopic opening of about 2 to 6 mm of diameter and allows for spatially and temporally resolving the streaming potential between the electrodes.

14. A method for detecting and mapping degradation in cartilage, comprising the steps of:
   a) applying at least two point electrodes against the cartilage;
   b) compressing said electrodes and cartilage together;
   c) measuring a streaming potential at each of said electrodes;
   d) analyzing and resolving the streaming potentials to obtain a map thereof; and
   e) interpreting said measured signals to determine the condition of the cartilage,
   wherein said at least two point electrodes allow for spatially resolving in two dimensions said streaming potentials.

15. The method of claim 14 further comprising the step of comparing the measured signals with stored signals.

16. The method of claim 14, wherein said step (b) comprises the steps of (i) positioning said electrodes against said cartilage, and (ii) applying a compressive force on said cartilage to press said cartilage against said electrodes.

17. A medical apparatus for early detection of degradation in cartilage, said apparatus comprising:
   a) at least two spaced apart point electrodes fixed to a solid surface and exposed for contact with a cartilage to be analyzed, each said electrodes measuring a streaming potential in such cartilage;
   b) means for compressing said electrodes and cartilage together selected from the group consisting of electromechanical means, piezoelectric means, and manual means, wherein said manual means comprise a defined abutment recessed from the electrodes for allowing said electrodes to be pressed in the cartilage until said cartilage abuts against said defined abutment;

c) signal processing means for processing signals received from the electrodes; and d) means for analytical interpretation of data received from said signal processing means, and wherein said medical apparatus allows for spatially and temporally resolving the streaming potentials measured between said electrodes.

18. A medical apparatus for early detection of degradation in cartilage, said apparatus comprising:

a) at least two spaced apart electrodes fixed to a solid surface exposed for contact with a cartilage to be analyzed, each said electrodes measuring a streaming potential in such cartilage;

b) means for compressing said electrodes and cartilage together selected from the group consisting of electro-mechanical means, piezo-electric means or manual means, wherein the electro-mechanical means comprise a precision actuator for positioning a load cell at a given height over the medical apparatus and depressing the cartilage against the electrodes;

c) signal processing means for processing signals received from the electrodes; and d) means for analytical interpretation of data received from said signal processing means, and wherein said medical apparatus allows for spatially and temporally resolving the streaming potentials measured between said electrodes.

19. A method for detecting and mapping degradation in cartilage, comprising the steps of:

a) applying at least two point electrodes against the cartilage;

b) compressing said electrodes and cartilage together;

c) measuring a streaming potential at each of said electrodes;

d) analyzing and resolving the streaming potentials to obtain a map thereof; and e) interpreting said measured signals to determine the condition of the cartilage.

wherein the step (b) comprises the steps of (i) providing said electrodes at a tip of a probe, and (ii) pressing said tip of said probe against said cartilage, and wherein said at least two point electrodes allows for spatially resolving the streaming potential measured at each of said electrodes.

* * * * *